United States Patent [19]

Riess

[11] 4,390,016
[45] Jun. 28, 1983

[54] PREFILLABLE HYPODERMIC SYRINGE AND METHOD OF ASSEMBLING THE SYRINGE

[75] Inventor: Gordon S. Riess, Beverly Hills, Calif.
[73] Assignee: Temp-Trak Inc., Beverly Hills, Calif.
[21] Appl. No.: 314,188
[22] Filed: Oct. 23, 1981
[51] Int. Cl.³ .............................................. A61M 5/00
[52] U.S. Cl. ..................................... 604/236; 604/194
[58] Field of Search .................. 128/215, 216, 218 R, 128/218 N, 218 D, 218 DA, 218 S, 220, 221, 234

[56] References Cited

U.S. PATENT DOCUMENTS

| | | | |
|---|---|---|---|
| 1,712,069 | 5/1929 | Cressler | 128/218 D |
| 3,107,785 | 10/1963 | Roehr | 128/218 N |
| 3,664,338 | 5/1972 | Knox et al. | 128/218 D |
| 4,148,316 | 4/1979 | Xanthopoulos | 128/221 |

*Primary Examiner*—John D. Yasko

*Attorney, Agent, or Firm*—Flehr, Hohbach, Test, Albritton & Herbert

[57] ABSTRACT

A prefillable type of hypodermic syringe assembly is disclosed herein. This assembly utilizes an open-ended glass barrel in combination with a rubber sealing bung located across the front end of the barrel and a rubber plunger slidably disposed within the barrel behind the sealing bung so as to define an internal medication chamber. In this way, medication stored within the chamber comes in contact with glass and rubber only until the syringe assembly is used. At that time, a syringe needle is placed in fluid communication with a cooperating opening through the sealing bung which serves to pass medication from the internal chamber to the needle. Until the syringe assembly is used, the sealing bung is maintained in a collapsed condition to close its through opening, thereby ensuring that only rubber and glass come in contact with the stored medication.

7 Claims, 5 Drawing Figures

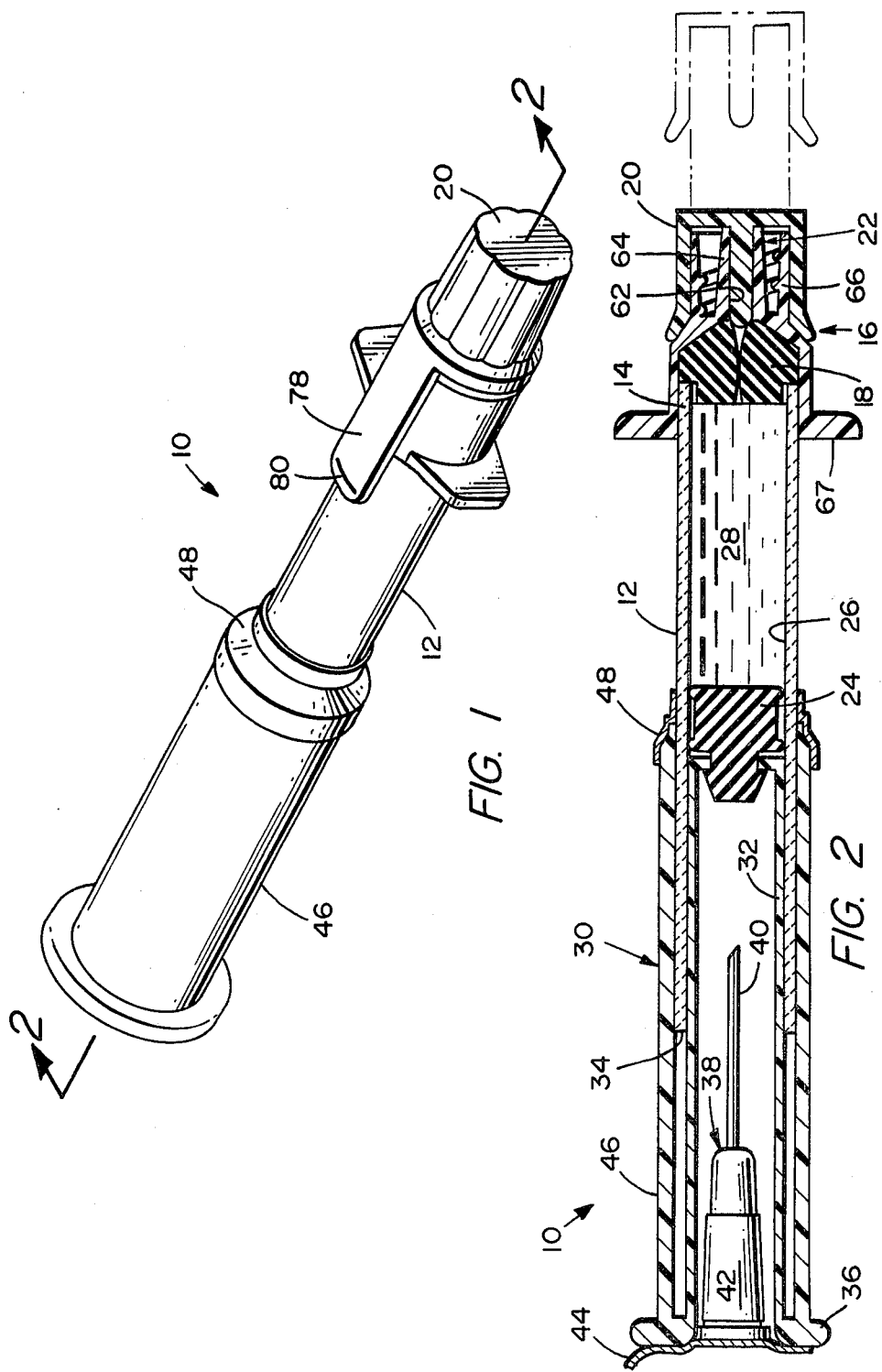

PREFILLABLE HYPODERMIC SYRINGE AND METHOD OF ASSEMBLING THE SYRINGE

The present invention relates generally to hypodermic syringes and more particularly to a specifically designed prefillable type of syringe and its method of assembly.

Hypodermic syringes for the injection of parenteral drugs are of two general types. There are extemporaneous hypodermic syringes which are filled by the user from a container of medication just prior to use and there are prefillable hypodermic syringes which are filled by the manufacturer, or at a centralized location, and delivered to the user in sealed packages. The use of prefilled syringes, as opposed to extemporaneous syringes, is increasing at a rapid rate because they offer significant advantages including better control over valuable drugs such as narcotics and dangerous toxic drugs. It is easier to account for drugs in prefilled syringes than in bulk and it is more difficult for an addict or a thief to withdraw the drug from its container. Other advantages include greater assurance that the person giving the injection has delivered precisely the correct amount. The pharmaceutical manufacturer can fill these syringes with very accurate dosages and, at the same time, they can provide tear strips or other sealing means for indicating whether or not prefilled syringes have been tampered with. The tear strips also may be used as a receipt, as evidence of use.

In addition, to these various advantages, there is less danger of contamination or cross-infection when using prefilled syringes as opposed to extemporaneous syringes which are typically filled from a common bottle. Also, prefilled syringes can be quicker and easier to use, thus saving valuable nursing time.

While prefillable syringes offer the various advantages recited above, in order to be practical they must be capable of containing medication for a reasonably long period. That is, they must display a reasonably long shelf life. The medication stored within the given prefilled syringe must not be contaminated or adulterated by the materials making up the syringe itself. Thus, in many cases, this means that the medication stored within the syringe can only be placed in direct contact with medical grade neutral glass and/or special rubber compounds formulated for compatibility with the particular medication. It is usually not acceptable for many medications to be placed in direct contact with plastic or steel containers for extended periods of time because of potential leaching of the plasticizers or oxidation of the metal.

Prefillable syringes currently in use are of three general types. First, there are types which include glass cartridges containing the medication. These cartridges are inserted into a metal or plastic holder, much as a shotgun shell is inserted into a shotgun. A second type of prefillable syringe presently in use closely resembles the conventional extemporaneous syringes except that its barrel is of glass rather than plastic. This particular type of syringe must be encased in a specially designed and formed container to prevent its plunger from being inadvertently depressed. A third type of prefillable syringe consists of a two-piece assembly in which the medication is included in one section which mates with a second section incorporating a double-ended needle. The two parts are screwed together or otherwise assembled immediately prior to use.

The prefillable syringes which are currently available are generally complicated in design and require special packaging. This results in undesirable cost and added bulk. They also may be time-consuming to assemble prior to use.

Particular disadvantages associated with certain ones of these syringes relate to the way in which they are filled. More specifically, certain types of prefillable syringes presently available include barrels which are filled from their back ends and then closed by means of associated plungers. However, it has been found to be difficult to close and seal a barrel of this type because of the air trapped therein as its plunger is inserted in place. This trapped air creates a pressure bubble which resists insertion of the plunger. Heretofore, one solution has been to fill syringes in a vacuum chamber. Another solution is to insert bleeder wires or microtubes between the plunger and the walls of the syringe barrel while the plunger is inserted therein, thereby allowing the trapped air to escape. The bleeder wires or tubes are then removed after the plunger is inserted in place.

All of the solutions recited above, that is, utilizing a vacuum chamber and the bleeder wire or microtubes, are relatively expensive and quite slow. Still another solution suggested heretofore has been to position the plunger within its associated barrel before the latter has been filled with medication. In this case, the barrel is filled with medication from its front end and then sealed utilizing a metal cap which is pressed or spun onto the front end of the barrel. This process is also relatively expensive and time consuming. Moreover, it exposes the stored medication to metal which, as stated previously, can be undesirable.

Accordingly, it is one object of the present invention to provide an uncomplicated and relatively inexpensive prefillable type of syringe which can be rapidly and reliably assembled and filled with medication for use in the future.

A more particular object of the present invention is to provide a prefillable hypodermic syringe which, when not in use, contains stored medication in a given chamber such that the medication comes in contact with glass and rubber only.

Another particular object of the present invention is to provide an uncomplicated and reliable way of filling the given medication chamber just recited from its front end rather than its back end and without using a vacuum chamber, bleeder wires, microtubes or metal caps.

Still another particular object of the present invention is to utilize a specifically designed rubber bung having a central through opening for sealing the front end of the medication chamber after the latter has been filled with medication.

Yet another specific object of the present invention is to provide an uncomplicated and reliable way of closing the opening in the last mentioned sealing bung when the syringe is not in use by using a plastic cap to accomplish this but without causing the medication within the chamber from coming into contact with the cap.

Still another object of the present invention is to provide a prefillable syringe design which permits high volume manufacturing and assembly at low cost, to make possible quick and easy use of the syringe by a nurse or technician and, at the same time, saving storage space.

As will be described in more detail hereinafter, the prefillable hypodermic syringe disclosed herein is one which includes an open ended barrel, preferably one constructed of medical grade neutral glass, having opposite front and back ends. A resilient sealing bung preferably constructed of medical grade rubber and including a through opening is connected with and closes the front end of the barrel, except for the through opening which serves to pass liquid medication therethrough when the syringe is in use. Until the syringe is used however, a cap is provided for closing the opening. The syringe also includes a needle and means for supporting the latter in fluid communication with the front end of the bung opening during operation of the syringe. A resilient plunger is disposed within the barrel and initially spaced rearwardly of the bung at a predetermined storage position, whereby to define a medication chamber therebetween. This plunger is moved from its storage position to a position adjacent the bung during operation of the syringe by suitable means disposed partially within and partially outside the barrel behind the plunger, whereby to cause liquid medication within the chamber to be forced through the bung opening and the needle when the latter is supported in fluid communication with the opening.

In a preferred and actual working embodiment of the present invention, the sealing bung and its associated cap are designed to cooperate with one another such that the latter engages the bung in a way which causes the bung to collapse upon itself sufficient to close its through opening without requiring the cap to close the opening directly. In this way, the cap, which is preferably constructed of plastic, does not come in contact with the stored medication. At the same time, the through opening can be used to allow air to escape from the medication chamber as the bung is assembled in place. On the other hand, the sealing bung and its associated cap can be preassembled together before the bung is connected with the barrel. In this case, the bung is provided with at least one but preferably a number of circumferentially spaced side slots which serve as vents for the air within the medication chamber as the bung and its cap are assembled in place. Once this occurs, the side slots are automatically sealed shut.

The various features just described and other features of the syringe disclosed herein will be described in more detail hereinafter in conjunction with the drawings wherein:

FIG. 1 is a perspective view of a prefillable hypodermic syringe designed in accordance with the present invention and shown in its filled, stored (rather than operating) position;

FIG. 2 is a longitudinal sectional view of the syringe of FIG. 1, taken generally along line 2—2 in FIG. 1;

Figure 3A:
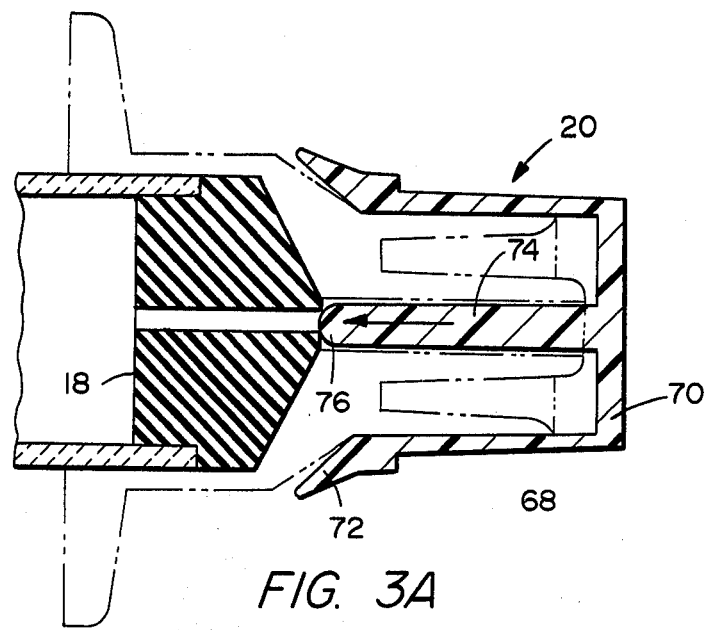
FIGS. 3A and 3B are enlarged cross sectional views of the front end of the syringe shown in FIGS. 1 and 2, particularly illustrating the way in which the front end is sealed prior to placing the syringe in use.

Turning now to the drawings, wherein like components are designated by like reference numerals throughout the various figures, attention is first directed to FIGS. 1 and 2. These figures illustrate a prefillable hypodermic syringe 10 which is designed in accordance with the present invention and which is shown in a prefilled condition for storage or shipment to the user. This syringe includes an open ended cylindrical barrel 12 which is preferably constructed of medical grade neutral glass. The front end 14 of barrel 12 carries an arrangement 16 which will be described hereinafter. For the moment, it suffices to say that this arrangement includes a sealing bung 18, an outer end cap 20 and an intermediate cap 22. The sealing bung and outer end cap cooperate with one another to seal the front end of barrel 12 after the syringe has been filled with medication and during storage thereof, and intermediate cap 22 serves to support a cooperating needle during operation of the syringe.

Referring specifically to FIG. 2, syringe 10 also includes a plunger 24, preferably of rubber, slidably disposed within barrel 12 behind arrangement 16 and in sealing engagement with the inner wall of the barrel. The plunger is shown in its stored position a predetermined distance rearwardly of the barrel's front end 14. The forwardmost end of the plunger and the rearwardmost end of bung 18 together with a section of barrel 12 therebetween define a medication chamber 26 which is shown filled with medication 28. As will be seen hereinafter, during operation of the syringe, the plunger is moved from its stored position to a position directly behind and adjacent to bung 18 for dispensing medication 28. In order to provide this movement of the plunger, syringe 10 includes an actuator generally indicated at 30 in FIG. 2. This actuator is shown including an innermost hollow, cylindrical tube 32 having a front end section slidably disposed within barrel 12 from its back end 34. The front end of tube 32 is located behind and connected with plunger 24 for moving the latter through chamber 26. The tube may be actuated for accomplishing this from its back end which extends out beyond the back end 34 of barrel 12 and which includes an enlarged end flange 36 for this purpose.

In the particular embodiment illustrated and in a preferred embodiment, tube 32 not only serves as an actuator but also as a means for storing a suitable syringe needle 38 when the syringe is not in use. This needle which is generally indicated at 38 may be of any conventional type compatible with the rest of the components making up the syringe and hence includes a needle cannula 40 and a hub 42. Once the needle is disposed within tube 32, the back end of the tube can be readily disengagably sealed in a sanitized fashion by any suitable means such as the bonding tab 44 shown in FIG. 2. Moreover, by providing actuator 30 with an outermost tube 46, the actuator can be used to disengagably secure plunger 24 in its stored position until the syringe is ready for use. More specifically, as illustrated in FIG. 2, outer tube 46 is disposed concentrically around inner tube 32 in spaced relationship therewith. The outer tube is fixedly connected to the inner tube at its rear end by means of flange 36 and its front end is open. In this way, the front end of the outer tube is able to extend around the outside of barrel 12 in approximate radial alignment with plunger 24. In a preferred embodiment, tubes 32 and 46 and flange 36 are integrally molded as a single unit serving as actuator 30.

Suitable tape, heat shrink material or the like, generally indicated at 48, is disposed around adjacent sections of tube 46 and barrel 12 including the juncture therebetween for preventing the outer tube and therefore the entire actuator from moving longitudinally relative to barrel 12. This, of course, locks the plunger 24 in place.

Figure 3B:
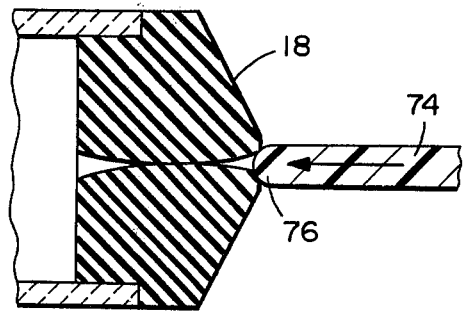
Figure 4:
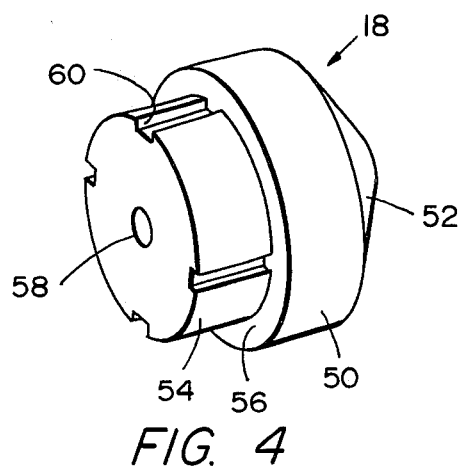
FIG. 4 is a perspective view of a sealing bung designed in accordance with the present invention and forming part of the syringe illustrated in FIGS. 1–3.

Turning to FIGS. 3 and 4, in conjunction with FIG. 2, attention is now directed to arrangement 16 which, as stated previously, includes bung 18, outer cap 20 and intermediate cap 22. As seen best in FIG. 4, bung 18 includes a forwardmost generally cylindrical section 50 having a tapered front end portion 52 and a rearward cylindrical section 54 smaller in diameter than the front section 50 concentric with and extending rearwardly from the back end of the front section. In this way, the front section 50 includes a rearwardly facing shoulder 56 extending entirely around section 54. As seen best in FIG. 3A, a through opening 58 is provided centrally through the two sections 50 and 54 from the rearwardmost end of the plunger to its tapered forwardmost end. In addition, as best seen in FIG. 4, the sealing bung embodiment shown there includes a plurality of longitudinally extending slots 60 extending the length of section 54 and into the latter from its outermost surface. As will be seen hereinafter, these slots may not be necessary. In either case, the sealing bung, like plunger 24, is preferably constructed of rubber, specifically rubber which is compatible with medication 28, that is, rubber of a type which does not degrade or otherwise adversely affect the medication when the two come in contact with one another.

As best seen in FIG. 2, intermediate cup 22 which is preferably of plastic includes a central cylindrical section 64 defining a through hole 62. Section 64 and a concentric outer skirt 66 are adapted to receive and support needle hub 42 in a sealed fashion so as to place needle 40 in communication with opening 58 and through hole 62. Section 64 and outer skirt 66 form a standard luer lock arrangement. The back end of cap 22 includes wings 67 serving as grippers for an operator's fingers. The overall intermediate cup 11 is preferably designed as a tear cap.

Referring specifically to FIG. 1 in conjunction with FIGS. 2 and 3A, end cap 20 is shown including a generally cylindrical and hollow main body 68 which is closed at its front end by means of end section 70. The back end of main body 68 is open and flares rearwardly and outwardly at 72. For reasons to be discussed below, cap 20 also includes a rodlike projection 74 fixedly connected to and extending rearwardly from a central point on front section 70 to a forwardmost point 76 located at the rear open end of main body 68. As seen only in FIG. 1, the cap 20 may also include an elongated tab 78 connected to and extending rearwardly from the back end of body 68.

The outer cap 20 is shown in FIGS. 1 and 2 in an assembled position in tight fitting relationship over and against the outer surface of skirt 66. At the same time, tab 78 extends rearwardly beyond wings 67 such that a rearwardmost end section engages an adjoining outer surface section of barrel 12. In this way, a breakable bond, for eample adhesive, generally indicated at 80 can be provided between these two sections and serves to indicate whether or not the syringe has been tampered with. In addition, projection 74 extends through opening 62 so that its forwardmost end 76 engages the front end of bung 18 directly around the front lip of opening 58. This, in turn, causes bung 18 to collapse upon itself sufficient to close opening 58 as shown in FIG. 2 and FIG. 3B. In this way, the mediaction 28 within chamber 26 comes in contact only with the sealing bung, plunger 24 and the inner surface of barrel 12. Since these components are made of medical grade neutral glass or compatible rubber, the medication can be stored within chamber 26 for relatively long periods without fear. Moreover, the end cap 20 may be made of plastic even though it is ultimately responsible for its closing opening 58.

With regard to tab 78, if chamber 28 is filled to less than one-third capacity, the tab could be bonded directly to the outer surrface of tube 46, thus eliminating the need for tape 48. On the other hand, the tape itself could be replaced with tape on heat-shrinkable material similar to tape 48 for bonding cap 20 to cap 22 (at the outermost juncture therebetween).

Having described syringe 10 in its prefilled, inoperative condition, attention is now directed to the way in which the syringe is initially assembled and filled with medication. At the outset, plunger 24 is placed in its storage position within barrel 12. The plunger is preferably first preassembled to the forwardmost end of tube 32. In this way, as plunger 24 is placed into its storage position, the outer tube 46 is positioned around and back end of the barrel in the manner shown in FIG. 2. At this time, the plunger 24 is preferably locked into place by means of material 48. It may also be held in place temporarily by the gripping jaws of the assembly and filling machine. The needle 38 may already be stored in tube 32 or this may be done in a later step. In any event, once plunger 24 is placed into its stored position, chamber 26 is filled from its front open end.

After chamber 26 has been filled, arrangement 16 is used to seal closed the front end of the chamber. Arrangement 16 can be placed into position in one of two ways. Either the seal bung 18 can be first assembled with the barrel apart from caps 20 and 22 or the three, that is, the two caps and the sealing bung, can first be assembled together so that the arrangement as a whole is then assembled with the barrel. In the first case, opening 62 remains open and may serve as a vent for any air in chamber 28 as the sealing bung is connected with barrel 12. More specifically, as rearward section 54 is inserted into the front end of barrel 12, any air between the liquid medication within chamber 26 and the back end of the bung is forced out into the ambient surroundings through opening 58. In this case, the slots 60 are not necessary and may be eliminated from the bung design. On the other hand, when the sealing bung and caps are preassembled together, opening 58 is closed before section 54 is inserted into barrel 12. Therefore, at least one slot 60 or other suitable means is necessary to vent the air from chamber 26. The slots serve this purpose and, at the same time, once the front end of the barrel 12 engages shoulder 56, the front end of the barrel is sealed closed even though the slots are present.

From the foregoing, it should be apparent that prefillable syringe 10 is relatively uncomplicated in design and quite capable of storing liquid medication such that the latter only comes in contact with glass and rubber. It should be equally apparent that the syringe is filled in an uncomplicated, reliable and rapid fashion without the need for a vacuum chamber, bleeder wires, microtubes or metal caps. Also, while the syringe has been shown in its preferred embodiment, it is to be understood that the the present invention is not limited to the particular configuration of each component making up the syringe.

What is claimed is:

1. A prefillable hypodermic syringe assembly, comprising:
   (a) an open ended barrel having opposite front and back ends;
   (b) a resilient sealing bung disengagably connected with and closing the front end of said barrel, said bung including an opening therethrough for the passage of liquid medication from within said barrel;

(c) cap means for closing said opening until said assembly is used, at which time said cap means can be removed, said cap means including means for engaging the front end of said bung so as to cause the latter to collapse upon itself sufficient to close said opening whereby to prevent any liquid medication within said chamber from coming in contact with said cap means;

(d) a hollow syringe needle;

(e) means for supporting said needle in fluid communication with the front end of said bung opening during use of the assembly;

(f) a resilient plunger disposed within said barrel and spaced rearwardly of said bung at a predetermined storage position, whereby to define a medication chamber therebetween; and (g) means disposed partially within and partially outside said barrel and engagable with said plunger for moving the latter from its storage position to a position adjacent said bung, whereby to cause liquid medication within said chamber to be forced through said bung opening and said needle when the latter is supported in fluid communication with said opening.

2. An assembly according to claim 1 wherein said barrel is constructed of glass and wherein said plunger and bung are constructed of rubber, whereby until said assembly is used any medication within said chamber comes in contact with glass and rubber only.

3. An assembly according to claim 1 wherein said bung includes a forwardmost section located outside and in sealing engagement against the front end of said barrel and a smaller rearwardmost portion extending into and against the inner surface of said barrel from its front end, said rearwardmost portion including at least one groove extending its entire length and opening out to the inner surface of said barrel.

4. An assembly according to claim 1 wherein said needle support means includes an intermediate luer cap disengagably connected over said bung and wherein said cap means includes an outer cap section disengagably connected over said intermediate cap, said outer cap sector including a rearward projection serving as said bung engaging means extending through said intermediate cap and engaging the front end of said bung across said opening, said bung being designed to collapse internally sufficient to close said opening as a result of the engagement of said projection.

5. An assembly according to claim 4 wherein said means engaging said plunger is cylindrical and hollow and includes disengagable means for closing its back end whereby to define a chamber therein, said last-mentioned chamber serving to contain said needle until the latter is ready for use.

6. A prefilled hypodermic syringe assembly, comprising:

(a) an elongated, open ended glass barrel having opposite front and back ends;

(b) a resilient rubber sealing bung having a central through opening, said bung being disengagably connected with and sealing closed the front end of said barrel, except for said opening, the latter serving to pass liquid medication therethrough from said barrel when said assembly is in use;

(c) an inner cap disengagably disposed over said sealing bung for supporting a hollow syringe needle in fluid communication with the front end of said bung opening during use of said syringe assembly, said inner cap including its own through hole coextensive with but larger than said bung opening;

(d) an inner plastic cap disengagably connected with said inner cap and including a rearwardly extending plastic projection extending through the through hole in said inner cap and in engagement with the front end of said sealing bung so as to cause the latter to collapse internally upon itself sufficient to close said opening;

(e) a resilient rubber plunger disposed within said barrel and spaced rearwardly of said bung at a predetermined storage position, whereby to define a medication chamber therebetween;

(f) a cylindrical plunger support disposed partially within and partially outside of said glass barrel and having an opened back end and a front end connected with said plunger for moving the latter from its storage position to a position adjacent said bung, whereby to cause any liquid medication within said chamber to be forced out through said bung opening and through a hollow syringe needle when the latter is supported by said inner cap in fluid communication with said opening;

(g) a hollow syringe needle disposed within said cylindrical plunger support;

(h) means for closing the back end of said cylindrical plunger support with said needle contained therein; and (i) means for disengagably maintaining said plunger support in a fixed position relative to said barrel such that in its said plunger remains in its predetermined storage position.

7. An assembly according to claim 6 wherein said sealing bung includes a forwardmost section located outside and in sealing engagement against the front end of said glass barrel and a smaller rearwardmost portion extending into and against the inner surface of said barrel from its front end, said rearwardmost portion including at least one groove extending its entire length and opening out to the inner surface of said barrel.

* * * * *